US006838285B2

(12) United States Patent
Farmer et al.

(10) Patent No.: US 6,838,285 B2
(45) Date of Patent: Jan. 4, 2005

(54) SITE SPECIFIC RECOMBINASE BASED METHOD FOR PRODUCING ADENOVIRAL VECTORS

(75) Inventors: Andrew Alan Farmer, Mountain View, CA (US); Thomas Patrick Quinn, Pacifica, CA (US)

(73) Assignee: Becton Dickinson, Franklin Lakes, NJ (US)

( * ) Notice: Subject to any disclaimer, the term of this patent is extended or adjusted under 35 U.S.C. 154(b) by 0 days.

(21) Appl. No.: 10/246,782

(22) Filed: Sep. 17, 2002

(65) Prior Publication Data

US 2003/0054555 A1 Mar. 20, 2003

Related U.S. Application Data

(60) Provisional application No. 60/323,536, filed on Sep. 18, 2001.

(51) Int. Cl.[7] .................. C12N 15/86; C12N 15/87; C12N 15/64; A01N 63/00; A01N 43/04
(52) U.S. Cl. .............. 435/456; 435/455; 435/462; 435/91.4; 435/91.41; 435/91.42; 424/93.2; 424/93.21; 514/44
(58) Field of Search .............. 435/69.1, 320.1, 435/325, 172.3, 235.1, 366, 456, 455, 462, 91.4, 91.41; 424/93.2, 93.21; 514/44

(56) References Cited

U.S. PATENT DOCUMENTS

| | | | |
|---|---|---|---|
| 5,354,678 A | 10/1994 | Lebkowski et al. | |
| 5,514,253 A | 5/1996 | Davis et al. | |
| 5,585,362 A | 12/1996 | Wilson et al. | |
| 5,589,377 A | 12/1996 | Lebkowski et al. | |
| 5,616,326 A | 4/1997 | Spibey | |
| 5,670,488 A | 9/1997 | Gregory et al. | |
| 5,700,470 A | 12/1997 | Saito et al. | |
| 5,731,172 A | 3/1998 | Saito et al. | |
| 5,747,072 A | 5/1998 | Davidson et al. | |
| 5,756,283 A | 5/1998 | Wilson et al. | |
| 5,789,390 A | 8/1998 | Descamps et al. | |
| 5,820,868 A | 10/1998 | Mittal et al. | |
| 5,837,484 A | 11/1998 | Trempe et al. | |
| 5,843,742 A | 12/1998 | Natsoulis et al. | |
| 5,851,806 A | 12/1998 | Kovesdi et al. | |
| 5,851,808 A | 12/1998 | Elledge et al. | |
| 5,858,351 A | 1/1999 | Podsakoff et al. | |
| 5,869,037 A | 2/1999 | Crystal et al. | |
| 5,871,982 A | 2/1999 | Wilson et al. | |
| 5,877,011 A | 3/1999 | Armentano et al. | |
| 5,880,102 A | 3/1999 | George et al. | |
| 5,885,808 A | 3/1999 | Spooner et al. | |
| 5,888,732 A | 3/1999 | Hartley et al. | |
| 5,891,690 A | 4/1999 | Massie | |
| 5,919,676 A | 7/1999 | Graham et al. | |
| 5,922,576 A | 7/1999 | He et al. | |
| 5,928,944 A | 7/1999 | Seth et al. | |
| 5,932,210 A | 8/1999 | Gregory et al. | |
| 5,952,221 A | 9/1999 | Kurtzman et al. | |
| 5,962,311 A | 10/1999 | Wickham et al. | |
| 5,962,313 A | 10/1999 | Podsakoff et al. | |
| 5,972,700 A | 10/1999 | Jacobs, Jr. et al. | |
| 6,080,569 A | 6/2000 | Graham et al. | |
| 6,120,764 A | 9/2000 | Graham et al. | |
| 6,228,646 B1 * | 5/2001 | Hardy | 435/455 |
| 6,274,354 B1 * | 8/2001 | Wilson et al. | 435/91.42 |
| 6,287,805 B1 | 9/2001 | Graham et al. | |
| 6,379,943 B1 * | 4/2002 | Graham et al. | 435/235.1 |
| 6,403,767 B1 | 6/2002 | Graham et al. | |
| 6,465,254 B1 * | 10/2002 | Saito et al. | 435/462 |
| 2002/0146392 A1 * | 10/2002 | Graham et al. | 424/93.1 |

FOREIGN PATENT DOCUMENTS

| | | |
|---|---|---|
| WO | WO 00/12687 | 3/2000 |
| WO | WO 00/30687 | 6/2000 |
| WO | WO01/05961 A1 | 1/2001 |

OTHER PUBLICATIONS

Kijima et al. Applicaitn of the Cre Recombinase/loxP System Further Enhances Antitumor Effects in Cell type–specific Gene Therapy against Carcinoembyronic Antigen–producing Cancer. Cancer Research 59, 4906–4911, Oct. 1, 1999.*

Aoki K. et al. Efficient Generation of Recombinant Adenoviral Vectors by Cre–lox Recombination in Vitro. Molecular Medicine. 5: pp224–231, 1999.*

Andre Lieber et al. "Recombinant Adenoviruses with Large Deletions Generated by Cre–Mediated Excision Exhibit Different Biological Properties Compared with First–generation Vectors In Vitro and In Vivo" *Journal of Virology*, Dec. 1996. p. 8944–8960, vol. 70 No. 12.

\* cited by examiner

*Primary Examiner*—Gerry Leffers
*Assistant Examiner*—Maria Marvich
(74) *Attorney, Agent, or Firm*—Stasia L. Ogden (57) ABSTRACT

Site-specific recombinase based methods for making a recombinant adenoviral genome, as well as kits for practicing the same and the recombinant adenovirus vectors produced thereby, are provided. In the subject methods, the subject genomes are prepared from donor and acceptor vectors that each include at least one site recombinase recognition site, where in certain preferred embodiments, one of the donor and acceptor vectors includes a single recombinase recognition site while the other includes two recombinase recognition sites. The acceptor vector includes an adenoviral genome having an E region deletion. The donor vector includes an insertion nucleic acid. In the subject methods, the donor and acceptor vectors are combined in the presence of a recombinase to produce an adenoviral genome that includes the insertion nucleic acid. The subject adenoviral genomes find use in a variety of applications, including as vectors for use in a variety of applications.

18 Claims, 3 Drawing Sheets

SITE SPECIFIC RECOMBINASE BASED METHOD FOR PRODUCING ADENOVIRAL VECTORS

CROSS-REFERENCE TO RELATED APPLICATIONS

Pursuant to 35 U.S.C. § 119(e), this application claims priority to the filing date of U.S. Provisional Patent Application Ser. No. 60/323,536 filed Sep. 18, 2001; the disclosure of which is herein incorporated by reference.

INTRODUCTION

1. Field of the Invention

The field of this invention is nucleic acid vectors, particularly adenoviral based vectors.

2. Background of the Invention

The introduction of an exogenous nucleic acid sequence (e.g. DNA) into a cell, a process known as "transformation," plays a major role in a variety of biotechnology and related applications, including research, synthetic and therapeutic applications. Research applications in which transformation plays a critical role include the production of transgenic cells and animals. Synthetic applications in which transformation plays a critical role include the production of peptides and proteins. Therapeutic applications in which transformation plays a key role include gene therapy applications. Because of the prevalent role transformation plays in the above and other applications, a variety of different transformation protocols have been developed.

A variety of viral based transformation protocols have been developed, in which a viral vector is employed to introduce exogenous DNA into a cell. Viral based vectors finding use include retroviral vectors, e.g. Maloney murine leukemia viral based vectors. Other viral based vectors that find use include, HSV derived vectors, sindbis derived vectors, etc. One type of viral vector of particular interest is the adenovirus derived vector.

Recombinant adenovirus vectors have been shown to have great promise for the gene transfer in basic research as well as clinical treatment of many diseases. They can transduce foreign genes efficiently into both cultured cells and many target organs in vivo.

There are more than forty different serotypes of adenovirus (Ad) identified. The Ad type 5 genome has been most commonly used to make recombinant Ad vector. The genome of human Ad is a linear 36 kb, double-stranded DNA genome that encodes more than 50 gene products.

In the first generation Ad vector, the early region 1 (E1) is replaced by the foreign gene and the virus propagated in an E1-transcomplementing cell line such as 293. By deleting E1 and early region 3 (E3) sequences up to about 8 kb of foreign gene can be inserted. However, in vitro manipulation of Ad DNA is difficult. Unique and useful restriction sites are limited because of the large size of the genome, making the construction of Ad vector relatively labor intensive. Two standard methods to make E1-deleted Ad vector have been developed::an in vitro ligation method and a homologous recombination method in, 293 cells.

The in vitro ligation method uses whole viral DNA genomes and the plasmid containing the left end of Ad with the right inverted terminal repeat (ITR), the packaging signal and E1A enhancer sequence (map unit; 0 to 1.3). After the gene of interest is inserted into the downstream of the viral sequence of the plasmid, the fragment containing viral sequence and gene of interest is excised and ligated to the unique ClaI site (map unit; 2.6), replacing a portion of the viral E1 region. Then, the ligated DNA is directly transfected into 293 cells to make recombinant virus. However, this method is rarely used today because the efficiency is low and the recombinant virus requires purification of contaminating wild type and transgene null viruses related to incomplete restriction digestion and self-religation.

One system using homologous recombination uses two plasmids with overlapping fragments that recombine in vivo. The first plasmid contains the entire Ad genome with a deletion of the DNA packaging and E1 region. The second plasmid contains right ITR, packaging signal and overlapping sequence with the first plasmid. After the gene of interest is introduced into the second plasmid, the two plasmids are co-transfected into 293 cells. The virus, which is produced by the recombination in 293 cells, is isolated through plaque purification. The major limitation to this approach is that the recombination event occurs at a low frequency.

Newer methods for adenoviral preparation are based on homologous recombination of two plasmids using yeast artificial chromosomes or bacteria. These methods, while more efficient, are more complex. The YAC system requires yeast culture and manipulation while the *E. coli* system requires three step transformations using an additional non-conventional host bacterial strain (BJ5183recBCsbcBC).

Another approach to the production of adenoviral vectors is direct, in-vitro ligation where the gene of interest is cloned into a shuttle vector and then excised and ligated into the recombinant adenovirus backbone using extremely rare restriction endonucleases. See e.g., WO 00/30687. While effective, there are disadvantages associated with this protocol, which disadvantages include: handling large viral DNA, inconsistent ligation products, and using an intermediate vector (shuttle) for transfer of the expression cassette.

Accordingly, there is continued interest in the development of new methods for preparing recombinant adenoviral vectors. Of particular interest would be the development of a method which is highly efficient and yet requires a minimum number of steps, where the method overcomes at least some of the disadvantages associated with the above described in vitro ligation protocol.

Relevant Literature

U.S. Patents of interest include: U.S. Pat. Nos. 5,962,313; 5,962,311; 5,952,221; 5,932,210; 5,928,944; 5,922,576; 5,919,676; 5,891,690; 5,885,808; 5,880,102; 5,877,011; 5,871,982; 5,869,037; 5,858,351; 5,851,806; 5,843,742; 5,837,484; 5,820,868; 5,789,390; 5,756,283; 5,747,072; 5,731,172; 5,700,470; 5,670,488; 5,616,326; 5,589,377; 5,585,362; and 5,354,678. See also WO 00/30687. Patents and published PCT applications describing site-specific recombinase based methods of transferring nucleic acids between vectors include: U.S. Pat. Nos. 5,851,808; 5,888,732; WO 00/12687 and WO 01/05961.

SUMMARY OF THE INVENTION

Site-specific recombinase based methods for making a recombinant adenoviral genome, as well as kits for practicing the same and the recombinant adenovirus vectors produced thereby, are provided. In the subject methods, the recombinant adenoviral genomes are prepared from donor and acceptor vectors that each include at least one site-specific recombinase recognition site, where in certain preferred embodiments, one of the donor and acceptor vectors includes a single recombinase recognition site while the other includes two recombinase recognition sites. The acceptor vector includes an adenoviral genome having an E region deletion. The donor vector includes an insertion nucleic acid. In the subject methods, the donor and acceptor vectors are combined in the presence of a recombinase to produce an adenoviral genome that includes the insertion nucleic acid located in the E region deletion, where at least one recombinase recognition site is also present in the E region deletion. The subject adenoviral genomes find use in a variety of applications, including as vectors for use in a variety of applications.

DEFINITIONS

As used herein, the term "donor construct" refers to a donor vector, i.e., a donor nucleic acid construct comprising two donor sequence-specific recombinase target sites each having a defined 5' to 3' orientation and placed in the donor construct such that they have the same 5' to 3' orientation, and a unique restriction enzyme site or polylinker, wherein the restriction enzyme site or polylinker is located 3' of the first-donor sequence-specific recombinase target site and 5' of the second-donor sequence-specific recombinase target site, and wherein the recombinase recognition sites are capable of recombining with each other.

As used herein, the term "first donor fragment" or "desired donor fragment" refers to the fragment produced when the donor construct is resolved, comprising a single sequence-specific recombinase target site having a 5' to 3' orientation wherein the 5' half of the single sequence-specific recombinase target site is derived from the 5' half of the second-donor sequence-specific recombinase target site in the donor construct and the 3' half of the single sequence-specific recombinase target site is derived from the 3' half of the first-donor sequence-specific recombinase target site of the donor construct, a polylinker or unique restriction site 3' to said sequence-specific recombinase target site, and the donor-partial selectable marker, or in certain embodiments, a donor-functional selectable marker. It is the first donor fragment that will combine with the acceptor construct to produce the final desired recombination product.

As used herein the term "second donor fragment" or "non-desired donor fragment" refers to the fragment produced when the donor construct is resolved, comprising a single sequence-specific recombination target site in which the 5' half is derived from the 5' half of the first-donor sequence-specific recombinase target site from the donor construct and the 3' half is derived from the 3' half of the second-donor sequence-specific recombinase target site from the donor construct.

As used herein, the term "acceptor construct" refers to an acceptor nucleic acid construct comprising at least one origin of replication, an acceptor sequence-specific recombinase target site having a defined 5' to 3' orientation, a first promoter located at the 5' end of the acceptor sequence-specific recombinase target site, and in certain embodiments, an acceptor-partial selectable marker.

As used herein, "final recombination constructs" refers to the recombination products produced when either the first donor fragment or the second donor fragment recombines with an acceptor construct, i.e., to generate expression vectors produced by the subject methods.

As used herein, "final desired recombination construct" refers to a recombination product produced when the first, or desired, donor fragment recombines with an acceptor construct, i.e., an expression construct.

The terms "sequence-specific recombinase" and "site-specific recombinase" refer to enzymes or recombinases that recognize and bind to a short nucleic acid site or "sequence-specific recombinase target site", i.e., a recombinase recognition site, and catalyze the recombination of nucleic acid in relation to these sites. These enzymes include recombinases, transposases and integrases.

The terms "sequence-specific recombinase target site", "site-specific recombinase target site", "sequence-specific target site" and "site-specific target site" refer to short nucleic acid sites or sequences, i.e., recombinase recognition sites, which are recognized by a sequence- or site-specific recombinase and which become the crossover regions during a site-specific recombination event. Examples of sequence-specific recombinase target sites include, but are not limited to, lox sites, att sites, dif sites and frt sites.

The term "lox site" as used herein refers to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as loxP511, loxP514, loxΔ86, loxΔ117, loxC2, loxP2, loxP3 and lox P23.

The term "frt site" as used herein refers to a nucleotide sequence at which the product of the FLP gene of the yeast 2 micron plasmid, FLP recombinase, can catalyze site-specific recombination.

The term "unique restriction enzyme site" indicates that the recognition sequence of a given restriction enzyme appears once within a nucleic acid molecule.

A restriction enzyme site or restriction site is said to be located "adjacent to the 3' end of a sequence-specific recombinase target site" if the restriction enzyme recognition site is located downstream of the 3' end of the sequence-specific recombinase target site. The adjacent restriction enzyme site may, but need not, be contiguous with the last or 3' most nucleotide comprising the sequence-specific recombinase target site.

The terms "polylinker" or "multiple cloning site" refer to a cluster of restriction enzyme sites, typically unique sites, on a nucleic acid construct that can be utilized for the insertion and/or excision of nucleic acid sequences, such as the coding region of a gene, loxP sites, etc.

The term "termination sequence" refers to a nucleic acid sequence which is recognized by the polymerase of a host cell and results in the termination of transcription. Prokaryotic termination sequences commonly comprise a GC-rich region that has a two-fold symmetry followed by an AT-rich sequence. A commonly used termination sequence is the T7 termination sequence. A variety of termination sequences are known in the art and may be employed in the nucleic acid constructs of the present invention, including the TINT3, TL13, TL2, TR1, TR2, and T6S termination signals derived from the bacteriophage lambda, and termination signals derived from bacterial genes, such as the trp gene of E. coli.

The terms "polyadenylation sequence" (also referred to as a "poly $A^+$ site" or "poly $A^+$ sequence") as used herein denotes a DNA sequence which directs both the termination and polyadenylation of the nascent RNA transcript. Efficient polyadenylation of the recombinant transcript is desirable, as transcripts lacking a poly $A^+$ tail are typically unstable and rapidly degraded. The poly $A^+$ signal utilized in an expression vector may be "heterologous" or "endogenous".

An endogenous poly $A^+$ signal is one that is found naturally at the 3' end of the coding region of a given gene in the genome. A heterologous poly $A^+$ signal is one which is isolated from one gene and placed 3' of another gene, e.g., coding sequence for a protein. A commonly used heterologous poly $A^+$ signal is the SV40 poly $A^+$ signal. The SV40 poly $A^+$ signal is contained on a 237 bp BamHI/Bc/l restriction fragment and directs both termination and polyadenylation; numerous vectors contain the SV40 poly $A^+$ signal. Another commonly used heterologous poly $A^+$ signal is derived from the bovine growth hormone (BGH) gene; the BGH poly $A^+$ signal is also available on a number of commercially available vectors. The poly $A^+$ signal from the Herpes simplex virus thymidine kinase (HSV tk) gene is also used as a poly $A^+$ signal on a number of commercial expression vectors.

As used herein, the terms "selectable marker" or "selectable marker gene" refer to a gene which encodes an enzymatic activity and confers the ability to grow in medium lacking what would otherwise be an essential nutrient; in addition, a selectable marker may confer upon the cell in which the selectable marker is expressed, resistance to an antibiotic or drug. A selectable marker may be used to confer a particular phenotype upon a host cell. When a host cell must express a selectable marker to grow in selective medium, the marker is said to be a positive selectable marker (e.g., antibiotic resistance genes which confer the ability to grow in the presence of the appropriate antibiotic). Selectable markers can also be used to select against host cells containing a particular gene; selectable markers used in this manner are referred to as negative selectable markers.

As used herein, the term "donor partial selectable marker" found in certainly embodiments of the subject invention refers to portion of a selectable marker gene encoded by the donor construct which is non-functional by itself, by which is meant that it must be positioned on a vector in operable relation with another element in order to be expressed. Examples of donor-partial selectable markers are coding sequences and promoter regions of complete selectable markers of functioning expression modules or cassettes.

As used herein, the term "donor-functional selectable marker" found in certain embodiments of the subject invention refers to a functional selectable marker gene encoded by the donor construct.

As used herein, the term "acceptor-partial selectable marker" found in certain embodiments of the subject invention refers to a portion of a selectable marker gene encoded by the acceptor construct which is non-functional by itself, as described above, e.g., a coding sequence or promoter by itself.

As used herein, the term "acceptor-functional selectable marker" found in certain embodiments of the subject invention refers to a functional selectable marker gene encoded by the acceptor construct.

As used herein, the term "recombinant-functional selectable marker" refers to the functional selectable marker gene created upon recombination between the donor construct and the acceptor construct which results in the adjacent placement of the donor-partial selectable marker and the acceptor-partial selectable marker, i.e., flanking either side of a recombinase site.

As used herein, the term "construct" is used in reference to nucleic acid molecules that transfer DNA segment(s) from one cell to another. The term "vector" is sometimes used interchangeably with "construct". The term "construct" includes circular nucleic acid constructs such as plasmid constructs, phagemid constructs, cosmid vectors, etc., as well as linear nucleic acid constructs including, but not limited to, PCR products. The nucleic acid construct may comprise expression signals such as a promoter and/or an enhancer inoperable linkage, and then is generally referred to as an "expression vector" or "expression. construct".

The term "expression construct" as used herein refers to an expression module or expression cassette made up of a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that the reading frame is maintained and a functional protein is produced.

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

Transformation of prokaryotic cells may be accomplished by a variety of means known in the art, including the treatment of host cells with $CaCl_2$ to make competent cells, electroporation, etc. Transfection of eukaryotic cells may be accomplished by a variety of means known in the art, including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "host" is meant to include not only prokaryotes, but also eukaryotes, such as yeast, plant and animal cells. A recombinant DNA molecule or gene can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Saccharomyces cerevisiae, Schizosaccharomyces pombe, Pichia pastoris*, mammalian cells and insect cells, and, plant cells, such as *Arabidopsis thaliana* and *Tobaccum nicotiana*.

As used herein, the terms "restriction endonucleases" and "restriction enzymes" refer to bacterial enzymes, each of which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule". The term "recombinant protein" or "recombinant polypeptide" as used herein refers to a protein molecule which is expressed from a recombinant DNA molecule.

The ribose sugar is a polar molecule, and therefore, DNA is referred to as having a 5' to 3', or 5' to 3', directionality. DNA is said to have "5' ends" and "3' ends" because mononucleotides are reacted to make oligonucleotides in a manner such that the 5' phosphate of one mononucleotide pentose ring is attached to the 3' oxygen of its neighbor via a phosphodiester linkage. Therefore, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also has a 5' to 3' orientation. In either a linear or circular DNA molecule, discrete elements are referred to as being "upstream" or "5'" of the "downstream" or "3'" elements. This terminology reflects the fact that DNA has an inherent 5' to 3' polarity, and transcription typically proceeds in a 5' to 3' fashion along the DNA strand. The promoter and enhancer elements which direct transcription of an operably linked coding region, or open reading frame, are generally located 5', or upstream, of the coding region. However, enhancer elements can exert their effect even when located 3' of the promoter and coding region. Transcription termination and polyadenylation signals are typically located 3' or downstream of the coding region.

The 3' end of a promoter is said to be located upstream of the 5' end of a sequence-specific recombinase target site when, moving in a 5' to 3' direction along the nucleic acid molecule, the 3' terminus of a promoter precedes the 5' end of the sequence-specific recombinase target site. When the acceptor construct is intended to permit the expression of a translation fusion, the 3' end of the promoter is located upstream of both the sequences encoding the amino-terminus of a fusion protein and the 5' end of the sequence-specific recombinase target site. Thus, the sequence-specific recombinase target site is located within the coding region of the fusion protein (i.e., located downstream of both the promoter and the sequences encoding the affinity domain, such as Gst).

As used herein, the term "adjacent", in the context of positioning of genetic elements in the constructs, shall mean within about 0 to 2500, sometimes 0 to 1000 bp and sometimes within about 0 to 500, 0 to 400, 0 to 300 or 0 to 200 bp.

A DNA "coding sequence" is a double-stranded DNA sequence which is transcribed and translated into a polypeptide in vivo when placed under the control of appropriate regulatory sequences: The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with proteins that can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence includes, at its 3' terminus, the transcription initiation site and extends upstream (in the 5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length.

As used herein, "an origin of replication" or "origin" refers to any sequence capable of directing replication of a DNA construct in a suitable prokaryotic or eukaryotic host (e.g., the ColE1 origin and its derivatives; the yeast $2\mu$ origin). Eukaryotic expression vectors may also contain "viral replicons" or "origins of replication". Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

As used herein, the terms "nucleic acid molecule encoding", "DNA sequence encoding", and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "gene" means the deoxyribonucleotide sequences comprising the coding region of a structural gene, i.e., the coding sequence for a protein or polypeptide of interest, including sequences located adjacent to the coding region on both the 5' and 3' ends for a distance of about 1 kb on either end, such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene which are transcribed into heteronuclear RNA (hnRNA); introns may contain regulatory elements such as enhancers. Introns are removed or "spliced out" from the nuclear or primary transcript; introns therefore are absent in the mature messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the term "purified" or "to purify" refers to the removal of contaminants from a sample. For example, recombinant Cre polypeptides are expressed in bacterial host cells (e.g., as a GST-Cre or $(HN)_6$-Cre fusion protein) and the Cre polypeptides are purified by the removal of host cell proteins; the percent of recombinant Cre polypeptides is thereby enriched or increased in the sample.

As used herein the term "portion" refers to a fraction of a sequence, gene or protein. "Portion" may comprise a fraction greater than half of the sequence, gene or protein, equal to half of the sequence, gene or protein or less than half of the sequence, gene or protein. Typically as used herein, two or more "portions" combine to comprise a whole sequence, gene or protein.

As used herein, the term "fusion protein" refers to a chimeric protein containing a protein of interest joined to an exogenous protein fragment. The fusion partner may enhance solubility of the protein of interest as expressed in a host cell, may provide an affinity tag to allow purification of the recombinant fusion protein from the host cell or culture supernatant, or both. If desired, the fusion protein may be removed from the protein of interest by a variety of enzymatic or chemical means known to the art.

DESCRIPTION OF THE SPECIFIC EMBODIMENTS

Site-specific recombinase based methods for making a recombinant adenoviral genome, as well as kits for practicing the same and the recombinant adenovirus vectors produced thereby, are provided. In the subject methods, the subject genomes are prepared from donor and acceptor vectors that each include at least one site recombinase recognition site, where in certain preferred embodiments, one of the donor and acceptor vectors includes a single recombinase recognition site while the other includes two recombinase recognition sites. The acceptor vector includes an adenoviral genome having an E region deletion. The donor vector includes an insertion nucleic acid. In the subject methods, the donor and acceptor vectors are combined in the presence of a recombinase to produce an adenoviral genome that includes the insertion nucleic acid located in the E region deletion, where at least one recombinase recognition site is also located in the E region deletion. The subject adenoviral genomes find use in a variety of applications, including as vectors for use in a variety of applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention.

Methods of Preparing the Subject Vectors

As summarized above, the invention provides methods of preparing adenoviral nucleic acid vectors. The subject methods are site-specific recombinase based methods of producing adenoviral nucleic acid vectors, i.e., recombinant adenoviral genomes. By "site-specific recombinase" based method is meant that the subject methods employ a recombinase mechanism to produce the subject recombinant adenoviral genomes. The recombinase mechanism that is employed in the subject methods is one in which a recombinase mediates the transfer of a nucleic acid from a donor to an acceptor vector, where the donor and acceptor vectors each include at least one recombinase recognition site. A variety of different site-specific recombinase systems suitable for transferring a nucleic acid from a donor to an acceptor vector are known and may be modified to be useful in the subject invention. Such systems include those described in U.S. Pat. Nos. 5,851,808; 5,888,732; 6,410,317; as well as WO 00/12687 and WO 01/05961, the disclosures of the priority documents of which are herein incorporated by reference.

In general, in addition to each including at least one recombinase recognition site, one of the donor and acceptor vectors includes adenoviral genome elements and the other includes the insertion nucleic acid to be transferred into the adenoviral genome to produce the recombinant adenoviral genome. In many embodiments, the donor vector includes the insertion nucleic acid and the acceptor vector includes the adenoviral genome elements. In other words, the acceptor vector includes the adenoviral genome sequences of interest and the donor vector includes the desired insertion nucleic acid, e.g., a non-adenoviral nucleic acid which is desired to be inserted into the adenoviral genome.

In many embodiments of interest, the donor and acceptor vectors are further characterized in that one of the donor and acceptor vectors includes only one recombinase recognition site, while the other of the donor and acceptor vectors includes two recombinase recognition sites. As mentioned above, in many embodiments, the donor vector includes two recombinase recognition sites while the acceptor vector includes a single recombinase recognition site. In an alternative embodiment, the donor vector includes a single recombinase recognition site while the acceptor vector includes two recombinase recognition sites. Such a system is described in U.S. Pat. No. 6,410,317, the disclosure of which is herein incorporated by reference.

The donor and acceptor vectors described generally above may be linear or circular, e.g., plasmids, and in many embodiments of the subject invention are plasmids. Where the donor and acceptor vectors are plasmids, the donor and acceptor vectors typically range in length from about .2 kb to 200 kb, usually from about 2 kb to 40 kb and more usually from about 2 kb to 10 kb.

The donor and acceptor vectors are further characterized in that all of the recombinase recognition sites on the donor and acceptor vectors must be recognized by the same recombinase and, in many embodiments, should be able to recombine with each other, but within this parameter they may be the same or different, but in many embodiments are usually the same. Recombinase recognition sites, i.e., sequence-specific recombinase target sites, of interest include: Cre recombinase activity recognized sites, e.g., loxP, loxP2, loxP511, loxP514, loxB, loxC2, loxL, loxR, loxΔ86, loxΔ117; att, dif; frt; and the like. The particular recombinase recognition site is chosen, at least in part, based on the nature of the recombinase to be employed in the subject methods.

The donor and acceptor vectors are now described in terms of the common embodiment in which the donor vector includes two site-specific recombinase recognition sites and the acceptor vector includes a single site-specific recombinase recognition site.

As mentioned above, in many embodiments of the subject invention, the acceptor vector employed in the subject methods is a vector that includes a single recombinase site. In these embodiments, the single recombinase site is flanked on one side by a promoter and on the other side, in certain preferred embodiments, by a portion of a selectable marker, e.g., a promoter or a coding sequence, where in many preferred embodiments described further below, this portion or sub-part of the selectable marker is a second promoter, e.g., a bacterial promoter. In these embodiments, the single recombinase site is flanked by two oppositely oriented promoters, where one of promoters drives expression of the gene of interest in the expression vector produced by the subject methods and the second promoter drives expression of the coding sequence of the recombinant-functional selectable marker in the expression vector produced by the subject methods. In these embodiments, the first promoter is a promoter that is capable of driving expression of the gene of interest in the expression vector, where representative promoters include, but are not limited to the CMV promoter, the tet-inducible promoter; retroviral LTR promoter/enhancer sequences, the TK promoter, bacterial promoters, e.g. the lac promoter, the $P_{LtetO-1}$ promoter; the yeast ADH promoter, tissue specific promoters, and the like. The distance between the first promoter and the recombinase site is one that allows for expression in the final expression vector, where the distance typically ranges from about 1 bp to 1000 bp, usually from about 10 bp to 500 bp. The second promoter is a promoter that is capable of driving expression of the recombinant-functional selectable marker, and is generally a bacterial promoter. Bacterial promoters of interest include, but are not limited to: the Ampicillin promoter, the lac promoter, the $P_{LtetO-1}$ promoter, the T7 promoter and the like. The distance between the bacterial promoter and the recombinase site is sufficient to provide for expression of the selectable marker in the expression vector and typically ranges from about 1 bp to 2.5 kb, usually from about 1 bp to 200 bp.

As indicated above, in yet other preferred embodiments the acceptor vector lacks the portion or subpart of the selectable marker. In these embodiments, the acceptor vector may be used with a donor vector that includes a complete positive selectable marker in the desired donor fragment flanked by the two recombinase sites, i.e., the donor vector portion located between the 3' end of the first recombinase site and the 5' end of the second recombinase site. Alternatively, the acceptor vector may be used with a donor vector that only includes a partial selectable positive marker, as described above, where the partial marker is nonetheless functional in the resultant expression vector.

The acceptor vector of the embodiments described above may include a number of additional components or elements which are requisite or desired depending on the nature of the expression vector to be produced from the acceptor vector. In many embodiments of the subject invention, the acceptor vector is an acceptor nucleic acid construct comprising: a) an origin of replication capable of replicating the final desired recombination construct or expression vector; b) an acceptor sequence-specific recombinase target site having a defined 5' to 3' orientation; c) a first promoter adjacent to the 5' end of the acceptor sequence-specific recombinase target site; and d) an acceptor-partial selectable marker, wherein the acceptor-partial selectable marker is capable of recombining with a donor-partial selectable marker from a donor construct (or first donor fragment, once the donor construct is resolved) so creating a recombinant-functional selectable marker in a final desired recombination construct. As in the donor construct, the acceptor construct is not limited by the nature of the sequence-specific recombinase target site employed, and in preferred embodiments the sequence-specific recombinase target site may be selected from the group consisting of loxP, loxP2, loxP511, loxP514, loxB, loxC2, loxL, loxR, loxΔ86, loxΔ117, loxP3, loxP23, att, dif, and frt. The acceptor sequence-specific recombinase target site from the acceptor construct does not have to be identical to those on the donor construct; however, the sequence-specific recombinase target sites on the acceptor and donor constructs must be able to recombine with each other.

In a preferred embodiment, the acceptor-partial selectable marker is a second promoter, wherein the second promoter is oriented such that its 5' to 3' orientation is opposite that of the acceptor sequence-specific recombinase target site and the first promoter, and wherein the 3' end of the second promoter is adjacent to the 3' end of the acceptor sequence-specific recombinase target site.

The acceptor construct is not limited by the nature of the origin of replication employed. A variety of origins of replication are known in the art and may be employed on the acceptor nucleic acid constructs of the present invention. Those skilled in the art know that the choice of origin depends on the application for which the acceptor construct is intended and/or the host strain in which the construct is to be propagated. In the case of the acceptor construct, the origin of replication is chosen appropriately such that both the acceptor construct and the final desired recombination construct will be able to replicate in the given host cell.

The acceptor construct also is not limited by the nature of the promoters employed. Those skilled in the art know that the choice of the promoter depends upon the type of host cell to be employed for expressing a gene(s) under the transcriptional control of the chosen promoter. A wide variety of promoters functional in viruses, prokaryotic cells and eukaryotic cells are known in the art and may be employed in the acceptor nucleic acid constructs of the present invention. In a preferred embodiment of the invention, the donor construct contains a gene or DNA sequences of interest and when the donor construct recombines with the acceptor construct, the first promoter of the acceptor construct is positioned such that it will drive expression of the gene or DNA sequences of interest. Thus, a promoter capable of driving the gene or DNA sequences of interest should be chosen for the first promoter. Further, in a preferred embodiment of the present invention, the acceptor-partial selectable marker is a promoter capable of driving the expression of the donor-partial selectable marker ORF from the donor construct (e.g., the promoter for the ampicillin gene from the plasmid pUC19) or a viral promoter including, but not limited to, the T7, T3, and Sp6 promoters.

In another preferred embodiment of the acceptor construct, the acceptor construct further includes an acceptor-functional selectable marker. The present invention is not limited by the nature of the acceptor-functional selectable marker chosen and the selectable marker gene may result in positive or negative selection. In a preferred embodiment, the acceptor-functional selectable marker gene is selected from the group consisting of the chloramphenicol resistance gene, the ampicillin resistance gene, the tetracycline resistance gene, the kanamycin resistance gene, the streptomycin resistance gene and the sacB gene.

In addition the above features, the acceptor vector also includes an adenoviral genome. By adenoviral genome is meant the genome of an adenovirus, where adenoviral type 5 genomes are of particular interest. A feature of the acceptor vector is that the adenoviral genome present in the vector includes an E gene deletion, such that the adenoviral genome is properly referred to as an E-gen deletion genome. By E gene deletion is meant a deletion or absence of a portion of the adenoviral genome where the adenoviral E genes (e.g., genomic coding sequences or domains that encode an E gene product) are present, e.g. E1, E2, E3, E4. The size of the E gene deletion of the subject first vector may vary, but in many embodiments typically ranges from about 1.0 to 25.0 kb, usually from about 1.0 to 12 kb and often from about 3 to 8 kb. In many embodiments, the E gene deletion includes a deletion of one of the E1, E3 and/or E4 genes, where in certain embodiments the deletion is characterized by a deletion of the E1 and E3 genes or a portion thereof, i.e. and E1/E3 deletion; and in other embodiments the deletion is a deletion of the E1 and E4 genes or a portion thereof, i.e. an E1/E4 deletion.

The acceptor vector is further characterized in that the recombinase recognition site is located in the E gene deletion region, such that the adenoviral genome produced by the subject methods is one in which an insertion nucleic acid is present in the E-gene deletion region.

In addition to the above components or features, the acceptor vector may further include restriction sites flanking either end of the adenoviral genome, which restriction sites are employed to excise the recombinant adenoviral genome from its vector, as described in greater detail infra. These restriction sites may be the same or different. Any convenient restriction site may be employed, so long as it is not found in the adenoviral genome present on the vector, where suitable sites include I-ceuI, SwaI, PI-SceI, I-SceI, I-PpoI, ClaI, AsuII (Csp45I) and the like.

The acceptor vector employed in the subject methods and described above may be fabricated using any convenient protocol. A suitable protocol for preparing various vectors which may serve as first vectors in the subject methods is provided in the experimental section, infra.

The donor vector employed in these embodiments of the subject methods is the vector that serves as the source of the non-adenoviral nucleic acid or insertion nucleic acid (i.e. the nucleic acid that is desired to be inserted into the adenoviral genome to produce the recombinant adenoviral genome and viral vectors of the subject invention). In other words, the non-adenoviral nucleic acid or insertion nucleic acid includes the nucleic acid which is desired to be inserted into the adenoviral genome of the first vector. Typically, the insertion sequence includes a multiple cloning site, i.e. a region having a plurality of different restriction endonuclease sites, where the number of different restriction endonuclease sites may vary greatly, but is often between about 1 to 20, usually between about 3 to 10. The insertion nucleic acid may or may not include a nucleic acid that encodes a product which is expressed under appropriate conditions. In other words, the insertion nucleic acid or non-adenoviral nucleic acid may or may not include a transgene. When present, this product encoding nucleic acid or gene is located in one of the restriction sites of the multiple cloning site of the insertion nucleic acid. The length of the insertion nucleic acid may vary, but in many typically ranges from about 1.0 to 35.0 kb, usually from about 1.0 to 12 kb and often from about 3 to 8 kb.

Depending on the ultimate use of the adenoviral vector, a variety of different features may be present in the insertion nucleic acid of the donor vector, in addition to those described above. In many embodiments, the insertion nucleic acid is characterized by the presence of at least one transcriptionally active gene. By transcriptionally active gene is meant a coding sequence that is capable of being expressed under intracellular conditions, e.g. a coding sequence in combination with any requisite expression regulatory elements that are required for expression in the intracellular environment of the target cell whose genome is modified by integration of the transposon. As such, the transcriptionally active genes of the subject vectors typically include a stretch of nucleotides or domain, i.e. expression module, that includes a coding sequence of nucleotidesin operational combination, i.e. operably linked, with requisite trascriptional mediation or regulatory element(s). Requisite transcriptional mediation elements that may be present in the expression module include promoters, enhancers, termination and polyadenylation signal elements, splicing signal elements, and the like.

Preferably, the expression module includes transcription regulatory elements that provide for expression of the gene in a broad host range. A variety of such combinations are known, where specific transcription regulatory elements include: SV40 elements, as described in Dijkema et al., EMBO J. (1985) 4:761; transcription regulatory elements derived from the LTR of the Rous sarcoma virus, as described in Gorman et al., Proc. Nat'l Acad. Sci USA (1982) 79:6777; transcription regulatory elements derived from the LTR of human cytomegalovirus (CMV), as described in Boshart et al., Cell (1985) 41:521; hsp70 promoters, (Levy-Holtzman, R. and I. Schechter (Biochim. Biophys. Acta (1995) 1263: 96–98) Presnail, J. K. and M. A. Hoy, (Exp. Appl. Acarol. (1994) 18: 301–308)) and the like.

In certain embodiments, the at least one transcriptionally active gene or expression module present in the insertion nucleic acid acts as a selectable marker. A variety of different genes have been employed as selectable markers, and the particular gene employed in the subject vectors as a selectable marker is chosen primarily as a matter of convenience. Known selectable marker genes include: the thimydine kinase gene, the dihydrofolate reductase gene, the xanthine-guanine phosporibosyl transferase gene, CAD, the adenosine deaminase gene, the asparagine synthetase gene, the antibiotic resistance genes, e.g. $tet^r$, $amp^r$, $Cm^r$ or cat, $kan^r$ or $neo^r$ (aminoglycoside phosphotransferase genes), the hygromycin B phosphotransferase gene, genes whose expression provides for the presence of a detectable product, either directly or indirectly, e.g. β-galactosidase, GFP, and the like.

In many embodiments, the at least one transcriptionally active gene or module encodes a protein that has therapeutic activity for the multicellular organism, where such include genes encoding the following products: factor VIII, factor IX, β-globin, low-density protein receptor, adenosine deaminase, purine nucleoside phosphorylase, sphingomyelinase, glucocerebrosidase, cystic fibrosis transmembrane regulator, α-antitrypsin, CD-18, ornithine transcarbamylase, arginosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides etc, and the like.

In the donor vector of these embodiments, in addition to the above described insertion nucleic acid, the donor vector includes two recombinase recognition sites, capable of recombining with each other, e.g., site 1A and site 1B, that flank or border the insertion nucleic acid (also properly referred to as the "donor domain," i.e., desired donor fragment), where this insertion nucleic acid is the portion of the vector that becomes part of the expression vector produced by the subject methods. In certain embodiments, the length of the donor domain (also described as insertion nucleic acid above) may vary, but in many embodiments ranges from 1 kb to 200 kb, usually from about 1 kb to 10 kb. The portion of the donor vector that is not part of this donor domain, i.e., the part that is 5' of site 1A and 3' of site 1B, is referred to herein for clarity as the non-donor domain of the donor vector.

The two recombinase recognition sites of the donor vector are characterized in that they are oriented in the same direction and are capable of recombining with each other. By oriented in the same direction it is meant that they have the same head to tail orientation. Thus, the orientation of site 1A is the same as the orientation of site 1B.

The donor domain flanked by the two recombinase recognition sites, i.e., the portion of the vector 3' of the first recombinase site 1A and 5' of the second recombinase site 1B, includes at least the following components: (a) at least one restriction site and (b) at least a portion of a selectable marker, e.g. a coding sequence, a promoter, or a complete selectable marker made up of a coding sequence and a promoter. The donor domain may include at least one restriction site or a plurality of distinct restriction sites, e.g., as found in a multiple cloning site or polylinker, where by restriction site is meant a stretch of nucleotides that has a sequence that is recognized and cleaved by a restriction endonuclease. Where a plurality of restriction sites are present in the donor domain, the number of distinct or different restriction sites typically ranges from about 2 to 5, usually from about 2 to 13.

In many embodiments, there are at least two restriction sites, which may or may not be identical depending on the particular protocol employed to produce the donor plasmid, that flank a nucleic acid which is a coding sequence for a protein of interest, where the protein of interest may or may not be known, e.g., it may be a known coding sequence for a known protein or polypeptide or a coding sequence for an as yet unidentified protein or polypeptide, such as where this nucleic acid of interest is a constituent of a library, as discussed in greater detail below. The length of this nucleic acid of interest nucleic acid may vary greatly, but generally ranges from about 18 bp to 20 kb, usually from about 100 bp to 10 kb and more usually from about 1 kb to 3 kb. At least one restriction site and this nucleic acid of interest nucleic acid, when present, are sufficiently close to the 3' end of the first flanking recombinase site, i.e., recombinase recognition site 1A, such that in the expression vector produced from the donor plasmid, expression of the coding sequence of the nucleic acid of interest is driven by a promoter positioned 5' of this first recombinase site. As such, the distance separating this restriction site/nucleic acid of interest nucleic acid from the recombinase site typically ranges from about 1 bp to 150 bp, usually from about 1 bp to 50 bp.

In a first preferred embodiment, the donor domain also generally includes a portion of a selectable marker. By portion of a selectable marker is meant a subpart of a selectable marker, e.g. a coding sequence or a promoter, which can be joined with a second subpart to produce a functioning selectable marker that confers some selectable phenotype on the host cell in which the expression vector produced by the subject methods is to be propagated. Examples of subparts of selectable markers are coding sequences and promoters. As such, in many embodiments, the portion of the selectable marker present on the donor domain is a coding sequence of a marker gene or a promoter capable of driving expression of the coding sequence of the marker gene, where in certain preferred embodiments, the coding sequence of a marker gene is the portion of the selectable marker present on the donor domain. Examples of coding sequences of interest include, but are not limited to, the coding sequences from the following marker genes: the chloramphenicol resistance gene, the ampicillin resistance gene, the tetracycline resistance gene, the kanamycin resistance gene, the streptomycin resistance gene and the SacB gene from *B. subtilis* encoding sucrase and conferring sucrose sensitivity; and the like. The promoter portions or sub-parts of this selectable marker are any convenient promoters capable of driving expression of the selectable marker in the expression vector produced by the subject methods, see infra, and in many embodiments are bacterial promoters, where particular promoters of interest include, but are not limited to: the Ampicillin resistance promoter, the inducible lac promoter, the tet-inducible promoter from pProTet ($P_{ltetO-1}$) available from CLONTECH, T7, T3, and SP6 promoters; and the like. The distance of this sub-part or portion of the selectable marker from the 3' end of the second recombinase recognition site, i.e., site 1B, is sufficient to provide for expression of the marker to occur in the final expression vector, where the other part of selectable marker that is required for efficient expression of the selectable marker is present on the other side, i.e., the 5' side of the adjacent recombinase recognition site. This distance typically ranges from about 1 bp to 2.5 kb, usually from about 1 bp to 500 bp.

The length of the donor domain flanked by the first and second recombinase sites of the donor plasmid, i.e., the length of the desired donor fragment, may vary greatly, so long as the above described components are present on the donor domain. Generally, the length is at least about 100 bp, usually at least about 500 bp and more usually at least about 900 bp, where the length may be as great as 100 kb or greater, but generally does not exceed about 20 kb and usually does not exceed about 10 kb. Typically, the length of the donor domain ranges from about 100 bp to 100 kb, usually from about 500 bp to 20 kb and more usually from about 900 bp to 10 kb.

In addition to the above described components, the donor vector may include a number of additional elements, where desired, that are present on the non-donor domain or non-desired donor fragment of the donor vector. For example, the non-donor domain generally includes an origin of replication. This origin of replication may be any convenient origin of replication or ori site, where a number of ori sites are known in the art, where particular sites of interest include, but are not limited to: ColE1 and its derivatives, pMB1, other origins that function in prokaryotic cells, the yeast 2 micron origin and the like. Also present on this nondonor domain of certain preferred embodiments is a selective marker gene that provides for negative selection of the non-donor domain under particular conditions, e.g., negative selection conditions. This marker is fully functional and therefor is made up of a coding sequence operably linked to an appropriate promoter, i.e., is provided by a functional expression module or cassette. Markers of interest that are capable of providing for this negative selection include, but are not limited to: SacB, providing sensitivity to sucrose; ccdB; and the like.

For purposes of amplification and selection, the donor vector may include one or more selectable marker genes, where genes of interest include genes that confer resistance to antibacterial agents. Representative marker genes include $tet^r$, $amp^r$, $Cm^r$, $cat^r$, $kan^r$, $neo^r$ and the like. In certain embodiments, the selectable marker gene of the second vector is different from the marker gene present on the first vector, e.g. where one desires to avoid an isolation step, as described in greater detail infra.

As with the first vector, the donor vector employed in the subject methods and described above may be fabricated using any convenient protocol. A suitable protocol for preparing various shuttle vectors which may serve as second vectors in the subject methods is provided in the experimental section, infra.

In practicing the subject methods, the above described donor and acceptor vectors are contacted with a recombinase under conditions sufficient for site specific recombination to occur, specifically under conditions sufficient for a recombinase mediated recombination event to occur that produces the desired recombinant adenoviral genome and vector comprising the same, where the production the adenoviral genome is accomplished without cutting or ligation of the donor and acceptor vectors with restriction endonucleases and nucleic acid ligases. The contact may occur under in vitro or in vivo conditions, as is desired and/or convenient.

In many embodiments, an aqueous reaction mixture is produced by combining the donor and acceptor vectors and the recombinase with water and other requisite and/or desired components to produce a reaction mixture that, under appropriate conditions, results in production of the desired recombinant adenoviral genome. The various components may be combined separately or simultaneously, depending on the nature of the particular component and how the components are combined. Conveniently, the components of the reaction mixture are combined in a suitable container. The amount of donor and acceptor vectors that are present in the reaction mixture are sufficient to provide for the desired production of the expression vector product, where the amounts of donor and acceptor vector may be the same or different, but are in many embodiments substantially the same if not the same. In many embodiments, the amount of donor and acceptor vector that is present in the reaction mixture ranges from about 50 ng to 2 μg, usually from about 100 ng to 500 ng and more usually from about 150 ng to 300 ng, for a reaction volume ranging from about 5 μl to 1000 μl, usually from about 10 μl to 50 μl.

The recombinase that is present in the reaction mixture is one that provides for recombination of the donor and acceptor vectors, i.e. one that recognizes the recombinase recognition sites on the donor and acceptor vectors. As such, the recombinase employed will vary, where representative recombinases include, but are not limited to: recombinases, transposes and integrases, where specific recombinases of interest include, but are not limited to: Cre recombinase (the cre gene has been cloned and expressed in a variety of hosts, and the enzyme can be purified to homogeneity using standard techniques known in the art—purified Cre protein is available commercially from Novagen); FLP recombinase of S. cerevisiae that recognizes the frt site; Int recombinase of bacteriophage Lambda that recognizes the aft site; xerC and xerD recombinases of E. coli, which together form a recombinase that recognizes the dif site. the Int protein from the Tn916 transposon; the Tn3 resolvase, the Hin recombinase; the Cin recombinase; the immunoglobulin recombinases; and the like. While the amount of recombinase present in the reaction mixture may vary depending on the particular recombinase employed, in many embodiments the amount ranges from about 0.1 units to 1250 units, usually from about 1 unit to 10 units and more usually from about 1 unit to 2 units, for the above described reaction volumes. The aqueous reaction mixture may include additional components, e.g., a reaction buffer or components thereof, e.g., buffering compounds, such as Tris-HCl; MES; sodium phosphate buffer, sodium acetate buffer; and the like, which are often present in amounts ranging from about 10 mM to 100 mM, usually from about 20 mM to 50 mM; monovalent ions, e.g., sodium, chloride, and the like, which are typically present in amounts ranging from about 10 mM to 500 mM, usually from about 30 mM to 150 mM; divalent cations, e.g., magnesium, calcium and the like, which are often present in amounts ranging from about 1 mM to 20 mM, usually from about 5 mM to 10 mM; and other components, e.g., BSA, EDTA, spermidine and the like; etc (where the above amount ranges are provided for the representative reaction volumes described above). As the reaction mixtures are aqueous reaction mixtures, they also include water.

The subject reaction mixtures are typically prepared at temperatures ranging from about 0–4° C., e.g., on ice, to minimize enzyme activity. Following reaction mixture preparation, the temperature of the reaction mixture is typically raised to a temperature that provides for optimum or maximal recombinase activity, and concomitantly expression vector production. Often, in this portion of the method the temperature will be raised to a temperature ranging from about 4° C. to 37° C.; usually from about 10° C. to 25° C., where the mixture will be maintained at this temperature for a period of time sufficient for the desired amount of expression vector production to occur, e.g., for a period of time ranging from about 5 mins to 60 mins, usually from about 10 mins to 15 mins. Following the incubation period, the reaction mixture is subjected to conditions sufficient to inactivate the recombinase, e.g., the temperature of the reaction mixture may be raised to a value ranging from about 65° C. to 70° C. for a period of time ranging from about 5 mins to 10 mins.

Alternatively, contact of the donor and acceptor vectors with the recombinase may occur in vivo, where the donor and acceptor vectors are introduced in a suitable host cell that expresses a recombinase. In this embodiment, the recombination between the donor and acceptor vectors may be accomplished in vivo using a host cell that transiently or constitutively expresses the appropriate site-specific recombinase (e.g., Cre recombinase expressed in the bacterial strain BNN132, available from CLONTECH). pDonor and pAcceptor, i.e., the donor and acceptor vectors respectively, are co-transformed into the host cell using a variety of methods known in the art (e.g., transformation of cells made competent by treatment with $CaCl_2$, electroporation, etc.). The co-transformed host cells are grown under conditions which select for the presence of the recombinant-functional selectable marker created by recombination of pDonor with the pAcceptor (e.g., growth in the presence of chloramphenicol when the pDonor vector contains all or part of the chloramphenicol resistance gene open reading frame and pAcceptor may also contain a promoter necessary for expression of the chloramphenicol open frame). Plasmid DNA is isolated from host cells which grow in the presence of the selective pressure and is subjected to restriction enzyme digestion to confirm that the desired recombination event has occurred.

The present invention also provides a method for the in vitro recombination of the subject recombinant adenoviral genome constructs, comprising the steps of: a) providing i) a donor nucleic acid construct comprising a donor-partial selectable marker, two donor sequence-specific recombinase target sites each having a defined 5' to 3' orientation and wherein the donor sequence-specific recombinase target sites are placed in the donor construct such that they have the same 5' to 3' orientation, and a unique restriction enzyme site or polylinker, the restriction enzyme site or polylinker being located 3' of the first-donor sequence-specific recombinase target site and 5' of the second-donor sequence-specific recombinase target site; (ii) an acceptor nucleic acid construct comprising an origin of replication, an acceptor sequence-specific recombinase target site having a defined 5' to 3' orientation, a first promoter adjacent to the 5' end of the acceptor sequence-specific recombinase target site, and an acceptor-partial selectable marker, wherein the acceptor-partial selectable marker is capable of recombining with the donor-partial selectable marker from the donor construct to create a recombinant-functional selectable marker in a final desired recombination construct; b) contacting the donor and acceptor constructs in vitro with a site-specific recombinase under conditions such that the desired donor fragment recombines with the acceptor construct to form a final desired recombination construct.

The present invention further provides a method for the recombination of nucleic acid constructs in a host to produce the subject recombinant adenoviral genome constructs, comprising the steps of: a) providing i) a donor nucleic acid construct comprising a donor-partial selectable marker, two donor sequence-specific recombinase target sites each having a defined 5' to 3' orientation and wherein the donor sequence-specific recombinase target sites are placed in the donor construct such that they have the same 5' to 3' orientation, and a unique restriction enzyme site or polylinker, the restriction enzyme site or polylinker located 3' of the first-donor sequence-specific recombinase target site and 5' of the second-donor sequence-specific recombinase target site; (ii) an acceptor nucleic acid construct comprising an origin of replication, an acceptor sequence-specific recombinase target site having a defined 5' to 3' orientation, a first promoter adjacent to the 5' end of the acceptor sequence-specific recombinase target site, and an acceptor-partial selectable marker, wherein the acceptor-partial selectable marker is capable of recombining with the donor-partial selectable marker from the donor to create a recombinant-functional selectable marker in a final desired recombination construct; and iii) a host cell expressing a site-specific recombinase; b) introducing the donor and acceptor constructs into the host cell under conditions such that the desired donor fragment recombines with the acceptor construct to form the final desired recombination construct which is capable of imparting the ability to the host cell to grow in selective growth medium.

The above step of combining the donor and acceptor vectors in the presence of a recombinase results in the production of a recombination composition that includes a recombinant adenoviral genome construct, i.e., a construct nucleic acid that includes the recombinant adenoviral genome of interest.

Recombinant Adenoviral Vectors

The above steps result in the production of a recombinant adenoviral vector that has an adenoviral genome with an E region deletion, e.g. a type 5 adenoviral genome with an E1/E3 deletion, with an insertion nucleic acid, e.g. a nucleic acid encoding a product, in the E deletion region of the adenoviral genome, where the vector is further characterized by the presence of at least one recombinase recognized site present in the E deletion region and, in many embodiments, two recombinase recognized sites flanking an insertion nucleic acid and located in the E deletion region. As mentioned above, while this resultant vector may be any suitable type of vector in principle, this vector is generally a plasmid. The E deletion region is characterized by the absence of at least part of at least one E gene, e.g. E1, E2, E3, E4, etc., where the length of the E deletion in many embodiments typically ranges from about 1.0 to 35.0 kb, usually from about 1.0 to 12 kb and often from about 3 to 8 kb. The size of the insertion nucleic acid present in the E deletion region in these embodiments typically ranges from about 1.0 to 35.0 kb, usually from about 1.0 to 12 kb and often from about 3 to 8 kb. The insertion nucleic acid may or may not encode a product. A number of different types of proteins may be encoded by the insertion sequence, where representative proteins are listed infra, and are also recited in the patents which are incorporated herein by reference in various locations of the specification. The recombinant adenoviral vectors are further characterized in that the adenoviral genome comprising the insertion nucleic acid is, in many embodiments, flanked by recombinase recognition sites.

The size of the resultant recombinant adenoviral vectors produced as described above may vary, depending on the nature of the vector. Where the vector is a plasmid, the size of the expression vector may range from about 3 kb to about 38 kb or higher, where the size ranges from about 33 to about 38 kb in many embodiments.

The resultant recombinant adenoviral vector is, in many embodiments, characterized in that it includes two recombinase recognition sites, i.e., a first and second recombinase recognition site, oriented in the same direction. The distance between the first and second recombinase sites, specifically the distance between the 3' end of the first recombinase site and the 5' end of the second recombinase site, ranges in many embodiments from about 100 bp to 100 kb, usually from about 500 bp to 20 kb, depending on whether the coding sequence of a protein of interest or just a restriction site/multiple cloning site, is present between the first and second recombinase recognition sites. The portion of the vector that lies in this inter recombinase region, i.e. 3' of the first recombinase site and 5' of the second recombinase site, typically makes up from about 2% to 85%, usually from about 20% to 60% of the entire expression vector.

In many embodiments, the recombinant adenoviral vector is further characterized in that 5' of the first recombinase site is a first promoter, 3' of the first recombinase site is at least one restriction site; and the second recombinase site located inside a functional selectable marker, i.e., it is flanked by disparate portions or sub-parts of a selectable marker expression module or cassette (e.g., a promoter and a coding sequence), where the second recombinase site is present between the two sub-parts of the selectable marker in a manner such that the selectable marker is functional, i.e., the coding sequence of the selectable marker is expressed. In other words the recombinant adenoviral vector includes a selectable marker expression cassette or module made up of a promoter and coding sequence that flank the second recombinase site. In many embodiments, the second recombinase site is flanked by a promoter on its 3' end and a coding sequence of the selectable marker on its 5' end. In this embodiment, the first and second promoters, located 5' of the first recombinase site and 3' of the second recombinase site, respectively, are oriented in opposite directions.

The recombinant adenoviral vector is further characterized by having at least one restriction site, and generally a multiple cloning site, located between the first and second recombinase sites. In many embodiments, located between the first and second recombinase sites, and flanked by two restriction sites, which may or may not be the same, is a nucleic acid of interest, i.e., gene of interest or insertion nucleic acid as described above, that includes a coding sequence for a protein of interest whose expression from the expression vector is desired. In these embodiments, the first promoter 5' of the first recombinase site and the coding sequence for the protein of interest are arranged on either side of the first recombinase site such that they form an expression module or cassette that expresses the encoded protein, i.e., the coding sequence and first promoter flank the first recombinase site in manner such that they are operably linked.

In addition to the above features, the recombinant adenoviral vector further includes at least one origin of replication that provides for replication in the host or hosts into which it is placed or transformed during use. Origins of replication of interest include, but are not limited to, those described above in connection with the donor and acceptor vectors.

In a specific embodiment, the recombinant adenoviral vector or final construct is characterized as follows—this final desired recombination construct comprises, in operable 5' to 3' order: a) a first promoter; b) a first-recombinant sequence-specific recombinase target site, wherein the 5' end of the first-recombinant sequence-specific recombinase target site is derived from the 5' end of the acceptor sequence-specific recombinase target site from the acceptor and the 3' end of the first-recombinant sequence-specific recombinase target site is derived from the 3' end of the first-donor sequence-specific recombinase target site of the donor construct; c) a unique restriction enzyme site or polylinker; d) the donor-partial selectable marker; e) a second-recombinant sequence-specific recombinase target site located within the recombinant-functional selectable marker gene and adjacent to the donor-partial selectable marker and the acceptor-partial selectable marker, wherein the 5' end of the second-recombinant sequence-specific recombinase target site is derived from the 5' end of the second-donor sequence-specific recombinase target site from the donor construct and the 3' end of the second-recombinant sequence-specific recombinase target site is derived from the 3' end of the acceptor sequence-specific recombinase target site of the acceptor construct; f) the acceptor-partial selectable marker, wherein the acceptor-partial selectable marker adjoins the donor-partial selectable marker to produce a newly-created recombinant-functional selectable marker; and, g) an origin of replication.

The recombinant adenoviral vectors produced according to the above described methods find use in, among other applications, the production of recombinant adenovirus particles or virions, which is turn find use in the transfer of nucleic acid into the genome of a cell, e.g. as is practiced in gene therapy applications, mutation analysis applications, and the like.

Recombinant Adenovirus and Methods for its Production

Also provided by the subject invention are recombinant adenoviruses and methods for their production. The recombinant adenoviruses of the subject invention are characterized by having an adenoviral genome in which at least a portion of the E region has been deleted and replaced with an insertion nucleic acid. The adenoviral genome of the subject viruses is further characterized by the presence of at least one recombinase recognition site, also typically located in the E region of the vector.

The subject viruses may be produced using the recombinant adenoviral vectors, described supra. To produce the subject viruses using the subject recombinant adenoviral vectors, a suitable host cell is transfected with a linearized double stranded DNA derived from the recombinant adenoviral vector and comprising the recombinant adenoviral genome. Generally, the linearized double stranded DNA that is employed in this step is produced by contacting the recombinant adenoviral vector with the restriction endonuclease(s) that cleave the sites flanking the genome in the vector. For example, where the adenoviral genome in the vector is flanked by PacI sites, the vector is contacted with PacI under conditions sufficient to cleave the vector and produce a linearized cleavage product that includes the recombinant adenoviral genome with the insertion sequence. Suitable host cells that are employed in the production of adenoviruses of the present invention are those that are transcomplementing for the E gene or genes which are missing/inactive in the recombinant adenoviral genome. The particular host cell employed varies depending on the nature of the E gene deletion region of the recombinant genome, but representative host cells that may be employed include: 293 cells, and the like. See also U.S. Pat. Nos. 5,928,944; 5,891,690; 5,872,005; 5,851,806; and 5,837,484; the disclosures of which are herein incorporated by reference. Transfection is carried out using any convenient protocol, where suitable protocols are known to those of skill in the art and a representative protocol is provided in the experimental section infra.

Following transfection, the transfected host cells are grown and recombinant adenovirus according to the subject invention is harvested therefrom, where any convenient protocol including standard protocols known to those of skill in the art may be employed for these steps. See e.g. the experimental section, infra.

Methods of Using the Subject Recombinant Adenoviruses

The subject recombinant adenoviruses can be used as vectors to stably insert a wide-variety of endogenous and/or exogenous nucleic acids into the genome of a target cell (exogenous means a nucleic acid having a sequence that is not present in the target cell while endogenous means a nucleic acid that pre-exists in the target cell, prior to insertion). In many embodiments, the sequence of nucleotides present in the exogenous nucleic acid will be one that is not found in the genome of the target cell. The subject methods can be used with a variety of target cells. Target cells with which the subject vectors may be employed are generally animal or plant cells, where in many embodiments the target cells are animal cells. Of particular interest in many embodiments is the use of the subject vectors to target vertebrate cells, particularly avian cells, e.g. chicken cells; mammalian cells, including murine, porcine, ovine, equine, rat, dog, cat, monkey, and human cells; and the like.

In the methods of the subject invention, the adenovirus vector is contacted with a target cell under conditions sufficient for the adenovirus to insert its recombinant genome into the target cell. Any convenient protocol may be employed, where the protocol may provide for in vitro or in vivo introduction of the genome into the target cell. For example, where the target cell is a cell of an organism which has been removed from the organism, the recombinant virus may be contacted with the cell under cell culture conditions permissive of viability of the target cell. Alternatively, where the target cell or cells are part of a multicellular organism, the adenoviral vector may be administered to the organism or host in a manner such that the virus enters the organism and inserts its genome into the target cell(s). For example, virus may be injected into the organism or host, contacted with a mucosal surface of the host and the like.

The subject methods of stable integration of exogenous nucleic acid into the genome of a target cell using the subject adenoviral vectors find use in a variety of applications in which the stable integration of an exogenous nucleic acid into a target cell genome is desired. Applications in which the subject vectors and methods find use include: research applications, polypeptide synthesis applications and therapeutic applications. Each of these representative categories of applications is described separately below in greater detail.

Research Applications

Examples of research applications in which the subject vectors find use include applications designed to characterize a particular gene. In such applications, the vector is employed to insert a gene of interest into a target cell and the resultant effect of the inserted gene on the cell's phenotype is observed. In this manner, information about the gene's activity and the nature of the product encoded thereby can be deduced. One can also employ the subject vectors to produce models in which overexpression and/or misexpression of a gene of interest is produced in a cell and the effects of this mutant expression pattern are observed.

One specific application of interest is the study of regulated gene expression. For example, one can include an inducible promoter, e.g., the tetracycline-inducible promoter, upstream of the recombinase recognition site, which feature allows regulated gene expression when the activator, e.g., the tet-transactivator (tTA or rtTA), is co-expressed in the cell. Users can express toxic and apoptotic genes at specific times.

One can also employ the subject vector to readily produce fusion proteins of a protein of interest fused to a fluorescent protein label domain. For example, with the addition of the loxP site in the adenovirus vector, creating fusion proteins with fluorescent protein tags is now extremely simple. It this scenario, the fluorescent protein is already in place in the vector and because of the mechanism of the recombinase, the gene of interest is inserted in the proper reading frame (once it is cloned into the donor properly). Both amino- and carboxy-terminal fusions can be made this way. These vectors allow end-users to follow their protein temporally as well as spatially using the proper filter sets.

Another application of interest is the complementation of packaging functions in the production of recombinant viruses. Since the subject viruses can be cloned into rather easily, they permit the expression of retroviral and lentiviral proteins for the purpose of packaging these recombinant viruses (or any recombinant virus for that matter). This application is unique in that packaging of these types recombinant RNA viruses (safely) requires that the expression constructs be placed in separate vectors to prevent recombination (as is done in current stable packaging cell lines). The high efficiency transfer and expression from the adenoviral vector will produce high quality retro- and lentiviral stocks in a transient manner.

The subject invention also finds use in tissue-specific expression applications. Since cloning procedures for adenovirus vector construction are simplified through the use of the above site specific recombinase system, one can now insert and test expression of tissue specific promoters. This application can be done by insertion of the promoter of interest into a loxP site upstream of one of the many markers available (fluorescent proteins, beta-galactosidase, luciferase etc,) within the adenoviral vector. The basic vector is also referred to as "promoterless". Once a promoter with desirable expression characteristics is found, a new vector can be easily created with a gene of interest The subject invention also finds use in the production of adenoviral libraries for expression cloning. Expression cloning allows a researcher to isolate a candidate gene that is able to complement a specific phenotype being studied in the lab. Important factors to be considered in these types of experiments are representation of the library, efficiency of delivery and screening methods. Prior to the subject invention, these vectors were not considered as candidates for library delivery. This was primarily due to the sheer size of the vector and the inability to maintain representation throughout the construction of the library. With the subject invention, transfer of a library (first constructed and tested in donor vector) is relatively efficient. Once the library is constructed, the end-user then infects their cells of interest, screens for the desired phenotype, and isolates the candidate gene using a variety of methods.

The subject invention also finds use in the production of antibodies. Adenovirus is a known adjuvant and can serve as a delivery vehicle into mice (or other organism) for the purpose of producing a humoral immune response and isolating antibodies specific for the protein of interest. The subject methods facilitate ease of cloning cDNA of interest.

The subject invention also finds use in integrated target rescue applications. If the researcher has an integrated target sequence flanked by loxP sites, then with the addition of Cre and another adenovirus containing a single loxP site, the target sequence will transfer to the rescuing adenoviral vector. Conversely, if there is a single loxP located in the genome, then delivery of a sequence to that set location can occur in the presence of Cre and a donating adenovirus with a sequence flanked by loxP sites.

Polypeptide Synthesis Applications

In addition to the above research applications, the subject vectors also find use in the synthesis of polypeptides, e.g. proteins of interest. In such applications, a vector that includes a gene encoding the polypeptide of interest in combination with requisite and/or desired expression regulatory sequences, e.g. promoters, etc., (i.e. an expression module) is introduced into the target cell that is to serve as an expression host for expression of the polypeptide. Following introduction and subsequent stable integration into the target cell genome, the targeted host cell is then maintained under conditions sufficient for expression of the integrated gene. Once the transformed host expressing the protein is prepared, the protein is then purified to produce the desired protein comprising composition. Any convenient protein purification procedures may be employed, where suitable protein purification methodologies are described in Guide to Protein Purification, (Deuthser ed.) (Academic, Press, 1990). For example, a lysate may be prepared from the expression host expressing the protein, and purified using HPLC, exclusion chromatography, gel electrophoresis, affinity chromatography, and the like.

Since adenovirus can infect cells at a high copy number, up to 100 copies/cell, protein production is extremely efficient. Adenoviral vectors can produce up to 20–30% of total cellular protein. Another added benefit is proper processing and folding that can only occur in mammalian cells. Inclusion of a signal peptide can allow the product to be harvested from the media in which the cells are grown. Also, the coding sequence for the gene of interest can be inserted using Cre-loxP mediated cloning and expressed with any number of tags (myc, 6xHN, His). These tags facilitate purification of the final product.

Therapeutic Applications

The subject vectors also find use in therapeutic applications, in which the vectors are employed to stably integrate a therapeutic nucleic acid, e.g. gene, into the genome of a target cell, i.e. gene therapy applications. The subject vectors may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer; and the like. Specific therapeutic genes for use in the treatment of genetic defect based disease conditions include genes encoding the following products: factor VIII, factor IX, β-globin, low-density protein receptor, adenosine deaminase, purine nucleoside phosphorylase, sphingomyelinase, glucocerebrosidase, cystic fibrosis transmembrane regulator, α-antitrypsin, CD-18, ornithine transcarbamylase, arginosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, and the like. Cancer therapeutic genes that may be delivered via the subject vectors include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like.

Uses of adenoviral vectors are further described in U.S. Pat. Nos. 5,962,313; 5,962,311; 5,952,221; 5,932,210; 5,928,944; 5,922,576; 5,919,676; 5,891,690; 5,885,808; 5,880,102; 5,877,011; 5,871,982; 5,869,037; 5,858,351; 5,851,806; 5,843,742; 5,837,484; 5,820,868; 5,789,390; 5,756,283; 5,747,072; 5,731,172; 5,700,470; 5,670,488; 5,616,326; 5,589,377; 5,585,362; 5,354,678; the disclosures of which are herein incorporated by reference.

Transgenic Cells and Non-Human Transgenic Animals

Also provided by the subject invention are transgenic cells and non-human transgenic animals. A feature of the subject cells is the presence of the subject recombinant adenovirus in the cell, e.g. either on a vector in the cell or stably integrated the cell's genome. Similarly, the transgenic animals of the subject invention are characterized by include at least one transgenic cell, as described supra.

Systems

Also provided are systems for use in practicing the subject methods. The subject systems at least include a donor vector and an acceptor vector as described above. In addition, the subject systems may include a recombinase which recognizes the recombinase sites present on the donor and acceptor vectors. The systems may also include, where desired, an E region transcomplementing cell, e.g., as described above. Other components of the subject systems include, but are not limited to: reaction buffer, controls, etc.

Libraries

Also provided are nucleic acid libraries cloned into donor and/or acceptor vectors of the subject invention. These nucleic acid libraries are made up of a plurality of individual donor/acceptor vectors where each distinct constituent member of the library has a different nucleic acid portion or component, e.g., genomic fragment, cDNA, of an original whole nucleic acid library, i.e., fragmented genome, cDNA collection generated from the total or partial mRNA of an mRNA sample, etc. In other words, the libraries of the subject invention are nucleic acid libraries cloned into donor or acceptor vectors according to the subject invention, where the nucleic acid libraries include, but are not limited to, genomic libraries, cDNA libraries, etc. Specific donor/acceptor libraries of interest include, but are not limited to: Human Brain Poly A+ RNA; Human Heart Poly A+ RNA; Human Kidney Poly A+ RNA; Human Liver Poly A+ RNA; Human Lung Poly A+ RNA; Human Pancreas Poly A+ RNA; Human Placenta Poly A+ RNA; Human Skeletal Muscle Poly A+ RNA; Human Testis Poly A+RNA; Human Prostate Poly A+RNA; analogous libraries from other species, e.g., rat, mouse, etc.; and the like. With donor libraries according to the subject invention, the subject methods permit the rapid exchange of either individual clones of interest, groups of clones or potentially an entire cDNA library into recombinant adenoviral expression vectors.

Kits

Also provided are kits for use in practicing the subject methods. The subject kits at least include at least a donor vector and an acceptor vector and a recombinase that recognizes the recombinase sites of the donor vector. The subject kits may further include other components that find use in the subject methods, e.g., recombinase, packaging cells, reaction buffers, positive controls, negative controls, etc.

The various components of the kit may be present in separate containers or certain compatible components may be precombined into a single container, as desired.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Vector Construction

A. Construction of pDNR-CMV-DsRed 3 Donor Vector

Figure 1:
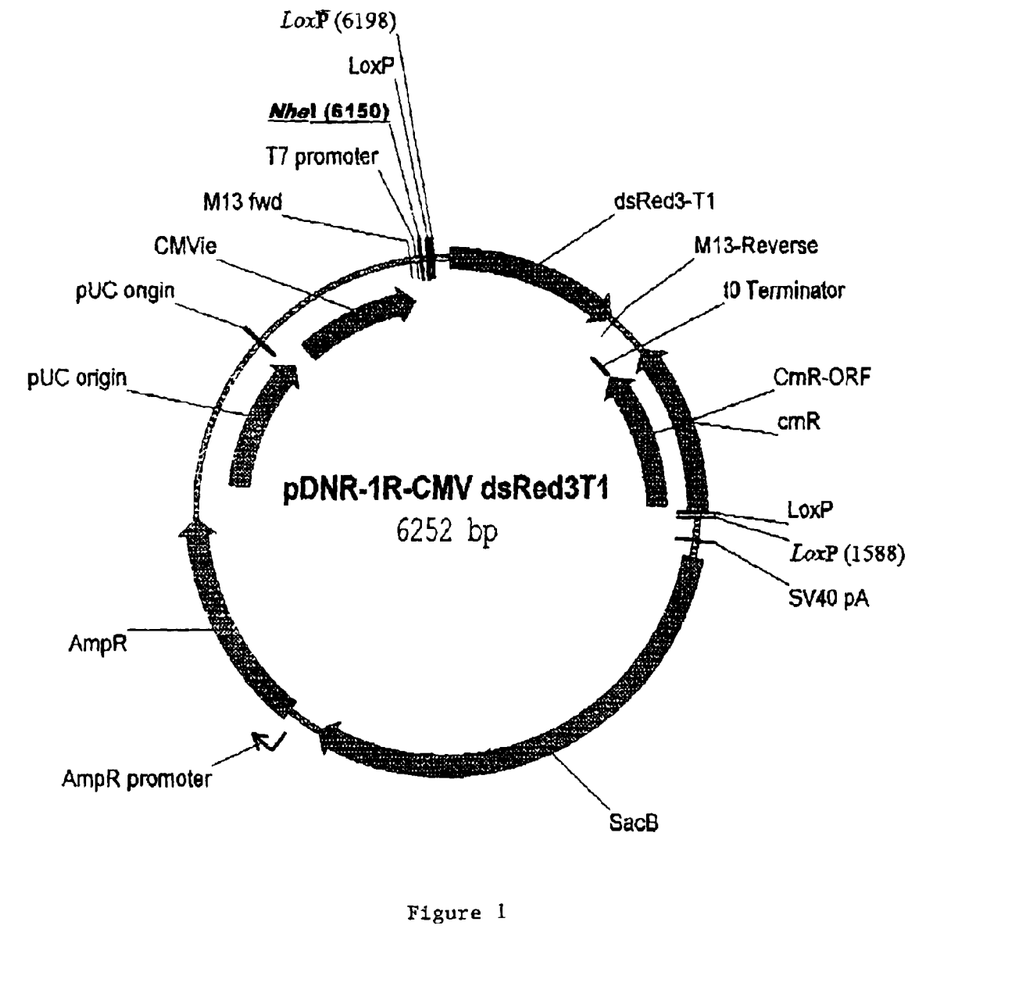
FIGS. 1 to 3 provide maps of different vectors employed in the Experimental Section, below.

To make the pDNR-CMV-DsRed 3 Donor vector (i.e., pDNR-1R-CMV dsRed3T1 of FIG. 1), the coding sequence for DsRed3 (obtained from Clontech Laboratories, Palo Alto, Calif. (Clontech Cat # 6695-1) was cloned into PDNR-CMV (obtained from Clontech Laboratories, Palo Alto, Calif. (Cat #1678-1)), using standard cloning techniques. See FIG. 1 for a map of this vector.

B. Construction of pLP-Adeno-X Acceptor Vector

Figure 2:
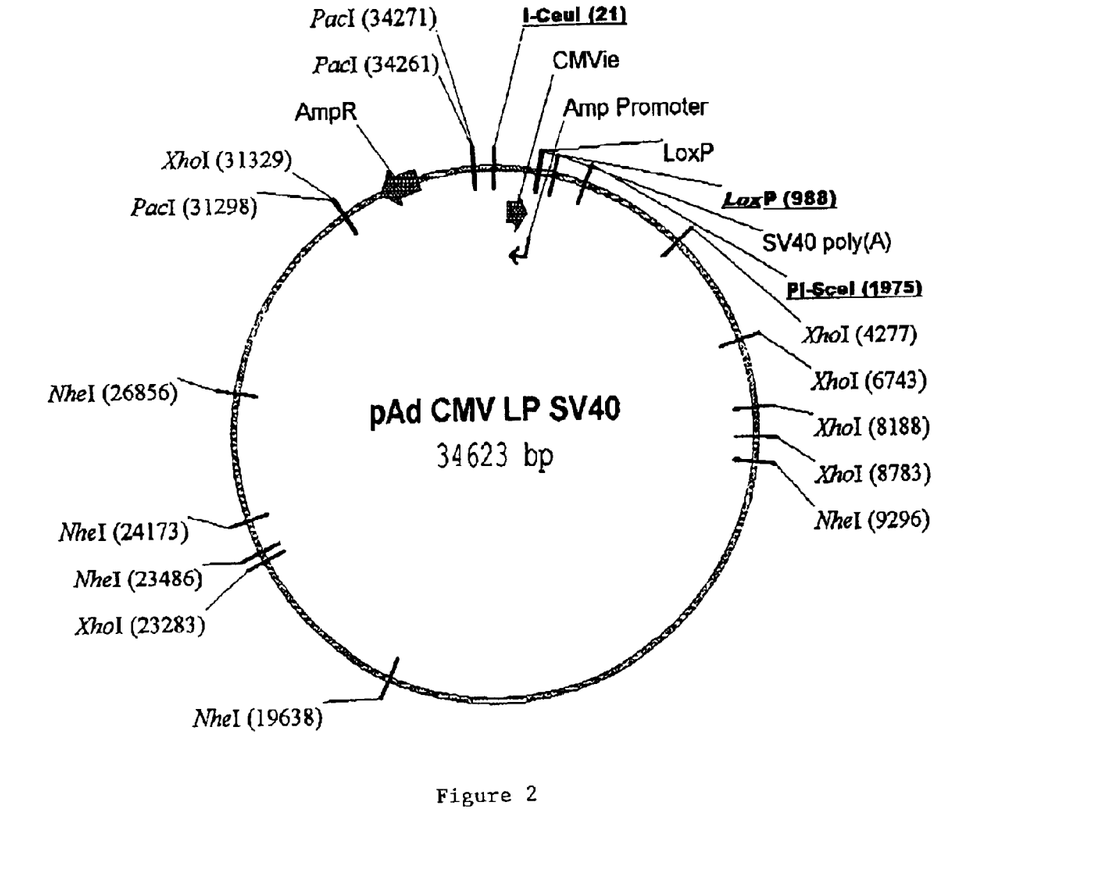

To make the pLP-Adeno-X acceptor vector (i.e., pAd CMV LP SV40 of FIG. 2), the Lox-promoter template from the Acceptor vector construction kit (Clontech Laboratories, Palo Alto, Calif. (Clontech Cat # K1690-1)) was cloned into the pshuttle Vector (Clontech Laboratories, Palo Alto, Calif. (Clontech Cat #K1650-1)) using the methods described in the Acceptor Vector construction user manual (available from Clontech Laboratories, Palo Alto, Calif.) to generate pLP-Shuttle. The LoxP-promoter cassette was then transferred from pLP-Shuttle to pAdeno-X (Clontech Laboratories, Palo Alto, Calif. (Clontech Cat # 1650-1)) using the methods described in the Adeno-X user manual (Clontech Laboratories, Palo Alto, Calif.) to generate pLP-Adeno-X. See FIG. 2 for a map of this vector.

Figure 3:
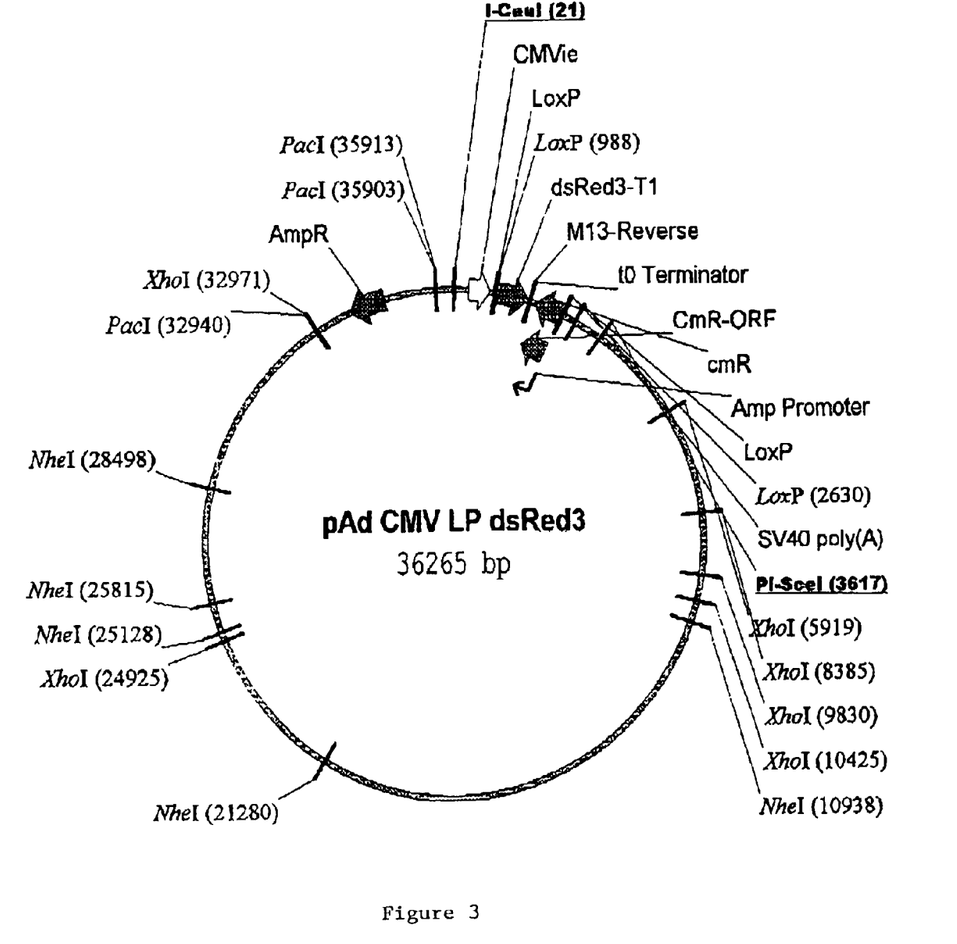

II. Construction of an Adenoviral Vector (i.e., pAd CMV LP SV40 of FIG. 3) for Expression of DsRed3 by in vitro Transfer using Cre from a DNR Vector to an Adenoviral Acceptor vector 200 ng pDNRCMV-dsRed3 (linearized by SacII and purified by Nucleospin Extraction Kit (Clontech Laboratories, Palo Alto, Calif.)), 400 ng AdCMVLP, 2 µl 10×Cre Buffer, and 2 µl 10×BSA were added together. PCR grade water was added to bring the final volume up to 19 µl and then 1 µl Cre recombinase was added. The resultant mixture was incubated for 15 minutes at room temperature and then heat inactivated for 5 minutes at 70° C. 1.5 µl of the Cre reaction was transformed by electroporation into 40 µl of DH10B ElectroMax, ice cold, 1.8 kV, 600 ohms, 15 microF. After pulsing, the transformed bacteria was incubated with shaking in 1 ml SOC at 37° C. for 1 hour, centrifuged, and cell pellet resuspended in 100 µl SOC medium (Clontech Laboratories, Palo Alto, Calif.). The resultant mixture was then plated on LB Miller Chloramphenicol 30 µg/ml+7% Sucrose 10 cm agar plate and incubated 37° C. for 24 hours.

10 colonies from the plate were each picked and resuspended in 20 µl sterile water. 10 µl was added to a 5 ml L B Miller Chloramphenicol 30 µg/ml+Ampicillin 100 µg/ml liquid culture and incubated 37° C. for 6 hours. The other 10 µl of each resuspended colony was added to a PCR reaction containing 1 µl 10 mM DNTPs, 1 µl each 20 µM primer PCP2 and CMV1, 2.5 µl 10×Titanium Buffer (Clontech Laboratories, Inc.), 0.5 µl 50×Titanium Polymerase (Clontech Laboratories, Inc.), and PCR Grade Water to bring the final volume to 25 µl. The PCR reaction was heated to 94° C. for 3 minutes and then cycled 20 times as follows: 94° C. for 15 seconds, 68° C. for 3 minutes. 3 µl of 10×DNA Loading Dye was then added to each reaction, 5 µl loaded onto a 1.5% Agarose gel, and run at 70V for 45 minutes. The gel was imaged under UV light and 8 out of 10 colonies were positive for the correct PCR product.

Two of the 5 ml cultures that corresponded to correct PCR reactions (samples 2 and 3) were each added to 100 ml L B Miller Chloramphenicol 30 µg/ml +Ampicillin 100 µg/ml liquid cultures and grown overnight shaking at 37° C. Plasmid DNA from the cultures was extracted using the Nucleobond Midi Purification Kit with the final pellet resuspended in 100 µl TE. Diagnostic digests of the DNA preps were done using XhoI, and PI-SceI I-CeuI. Both preps followed the expected banding patterns.

III. Linearization of Adenoviral Expression Vector and Transfection into 293 Cells to Generate a Viral Stock 10 µg each were then digested for 2 hours with 5 µl PacI in appropriate buffer at a final volume of 50 µl. The PacI digests were then purified by Phenol-Chloroform extraction and Ethanol precipitation. After purification, the linearized preps were transfected into HEK293 cells and grown for 9 days when 100% CPE occured.

IV. Amplification, Titration and Expression Analysis of the Viral Stock Expressing DsRed3

The rescued virus was used to infect 1E+8HEK293 cells and resulted in 100% CPE in 2 days. The amplified virus was purified using the Adeno-X Virus Purification Kit (Clontech Laboratories, Inc.) and then titrated by the Adeno-X Rapid Titer Kit. The resulting titer was 1.5 ml at 2.0E+9 ifu/ml. Prior to fixation, the cells infected for the titration were imaged under UV light and showed strong Red fluorescence.

The benefits of the subject methods of adenoviral construction are many. In the subject methods, the adenoviral vector remains closed-circular as opposed to what occurs in the the ligation-based strategy. This feature minimizes the handling of a large (36 kb) plasmid that can cause shearing and loss of product. Since the recombinant vector is completed in the tube in which the reaction took place, transformation into a single bacterial strain and isolation of positive clone yields DNA for transfection and virus production. This feature is unlike the bacteria-based recombination method which requires two strains. Also, once the clone is isolated using the subject system, it nearly eliminates the need to do plaque purification of the final viral product (purification may still be desirable for in-vivo use). With the 293-based recombination, multiple plaque purifications are a requirement of the system. With the ease of cloning the subject system affords the adenoviral expression system, many technologies can now be applied to this system. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of preparing a recombinant adenoviral genome having an insertion nucleic acid located in an early (E) gene region of said genome, said method comprising:
   (a) providing a donor vector comprising an insertion nucleic acid and a first and second recombinase recognition site that are able to recombine with each other;
   (b) providing an acceptor vector comprising an adenoviral genome having an E region deletion and at least one recombinase recognition site located in E region deletion;
   (c) combining said donor and acceptor vectors with a recombinase that recognizes said donor and acceptor recombinase recognition sites to produce an adenoviral genome having an insertion nucleic acid located in an E gene region of said genome.

2. The method according to claim 1, wherein said first and second recombinase recognition sites flank said insertion nucleic acid.

3. The method according to claim 1, wherein said acceptor vector comprises a single recombinase recognition site.

4. The method according to claim 1, wherein said donor and acceptor vectors are plasmids.

5. The method according to claim 1, wherein said E region deletion comprises a deletion of at least a portion of at least one of E1, E3 and E4 region.

6. The method according to claim 1, wherein said recombinase is a Cre recombinase.

7. The method according to claim 1, wherein said recombinase recognition sites are lox sites.

8. The method according to claim 1, wherein said adenoviral genome is present on the acceptor plasmid.

9. A method of producing a recombinant adenovirus having a genome having an insertion nucleic acid located in an E gene region of said genome, said method comprising:
   (a) preparing a recombinant adenoviral genome having an insertion nucleic acid located in an E gene region of said genome by:
      (i) providing a donor vector comprising an insertion nucleic acid and first and second recombinase recognition sites that are able to recombine with each other;
      (ii) providing an acceptor vector comprising an adenoviral genome having an E gene deletion and at least one recombinase recognition site; and
      (iii) combining said donor and acceptor vectors with a recombinase that recognizes said donor and acceptor recombinase recognition sites to produce an adenoviral genome having an insertion nucleic acid located in an E gene region of said genome;
   (b) transforming a cell that is transcomplementing for any inactivated E genes of said E gene region with said adenoviral genome; and
   (c) maintaining said transformed cell under conditions sufficient for virus to be produced so as to produce said recombinant adenovirus having a genome having an insertion nucleic acid located in an E gene region of said genome.

10. A kit for use in preparing a recombinant adenovirus, said kit comprising:
    (a) a donor vector comprising an insertion nucleic acid and a first and second recombinase recognition site that are able to recombine with each other, and
    (b) an acceptor vector comprising an adenoviral genome comprising an E gene deletion region and at least one recombinase recognition site located in said E gene deletion region.

11. The kit according to claim 10, wherein said first and second recombinase recognition sites flank said insertion nucleic acid.

12. The kit according to claim 10, wherein said acceptor vector comprises a single recombinase recognition site.

13. The kit according to claim 10, wherein said donor and acceptor vectors are plasmids.

14. The kit according to claim 13, wherein said kit further comprises a recombinase.

15. The kit according to claim 10, wherein said recombinase is Cre.

16. The kit according to claim 15, wherein said recombinase recognition sites are lox site.

17. The kit according to claim 10, wherein said kit further comprises a cell that is transcomplementing for any inactivated E genes of said E gene region of said adenoviral genome.

18. A system for use in preparing a recombinant adenovirus, said system comprising:
    (a) a donor vector comprising an insertion nucleic acid and first and second recombinase recognition sites that are able to recombine with each other;
    (b) an acceptor vector comprising an adenoviral genome comprising;
    (c) an E gene deletion region and at least one recombinase recognition site located in said E gene deletion region;
    (d) a recombinase; and
    (e) a cell that is transcomplementing for any inactivated E genes of said E gene region of said adenoviral genome.

* * * * *

UNITED STATES PATENT AND TRADEMARK OFFICE
CERTIFICATE OF CORRECTION

PATENT NO. : 6,838,285 B2
DATED : January 4, 2005
INVENTOR(S) : Farmer, Andrew Alan et al.

It is certified that error appears in the above-identified patent and that said Letters Patent is hereby corrected as shown below:

<u>Title page,</u>
Item [73], Assignee, should read -- Clontech Laboratories, Inc.,
Palo Alto, California --.

Signed and Sealed this

Seventh Day of March, 2006

JON W. DUDAS
*Director of the United States Patent and Trademark Office*